United States Patent
Polat et al.

(10) Patent No.: US 10,433,886 B2
(45) Date of Patent: Oct. 8, 2019

(54) TELESCOPIC NAIL

(71) Applicant: TST RAKOR VE TIBBI ALETLER SANAYI VE TICARET LIMITED ŞIRKETI, Pendik-Istanbul (TR)

(72) Inventors: Ahmet Fethi Polat, Pendik-Istanbul (TR); Muharrem Inan, Kartal Istanbul (TR)

(73) Assignee: TST RAKOR VE TIBBI ALETLER SANAYI VE TICARET LIMIT, Istanbul (TR)

(*) Notice: Subject to any disclaimer, the term of this patent is extended or adjusted under 35 U.S.C. 154(b) by 0 days.

(21) Appl. No.: 15/559,783

(22) PCT Filed: Apr. 29, 2016

(86) PCT No.: PCT/TR2016/050130
§ 371 (c)(1),
(2) Date: Sep. 19, 2017

(87) PCT Pub. No.: WO2016/175729
PCT Pub. Date: Nov. 3, 2016

(65) Prior Publication Data
US 2018/0064475 A1 Mar. 8, 2018

(30) Foreign Application Priority Data
Apr. 29, 2015 (TR) ................ 2015 05232

(51) Int. Cl.
*A61B 17/72* (2006.01)
*A61B 17/86* (2006.01)

(52) U.S. Cl.
CPC ........... *A61B 17/725* (2013.01); *A61B 17/72* (2013.01); *A61B 17/7283* (2013.01); *A61B 17/869* (2013.01); *A61B 17/7216* (2013.01)

(58) Field of Classification Search
CPC ....... A61B 17/60; A61B 17/66; A61B 17/663; A61B 17/666; A61B 17/7013;
(Continued)

(56) References Cited

U.S. PATENT DOCUMENTS 2,672,861 A * 3/1954 Jonas .................. A61B 17/72
606/63
4,644,943 A * 2/1987 Thompson ............. A61B 17/88
606/64
(Continued)

FOREIGN PATENT DOCUMENTS

DE 102014119011 A1 * 6/2016 ............. A61B 17/64
FR 2749157 A1 * 12/1997 ............. A61B 17/72
FR 2831421 1/2004

OTHER PUBLICATIONS

English translation of FR2749157.*
Translation of DE 102014119011.*

*Primary Examiner* — Lynnsy M Summitt
(74) *Attorney, Agent, or Firm* — Oppenhuizen Law PLC; David L. Oppenhuizen

(57) ABSTRACT

An intramedullary nail for surgical use with pediatric patients aged 18 months and older who are diagnosed with Osteogenesis Imperfecta. The intramedullary nail is used to correct deformity, stabilize fractures, and to prevent fractures. The intramedullary nail includes male components that can be nested with a straight formed female component. The angled female component has a telescopic structure that grows together with the child's bone without hindering growth. The intramedullary nail also includes at least one telescopic nail with a corkscrew tip that provides minimal damage.

11 Claims, 4 Drawing Sheets

(58) Field of Classification Search
CPC ............ A61B 17/7014; A61B 17/7016; A61B 17/7017; A61B 17/7019; A61B 17/72; A61B 17/7216; A61B 17/7233; A61B 17/8004; A61B 17/8009; A61B 17/8023
See application file for complete search history.

(56) References Cited

U.S. PATENT DOCUMENTS

| | | | | |
|---|---|---|---|---|
| 5,074,882 A * | 12/1991 | Grammont | ......... | A61B 17/7216 606/63 |
| 5,100,405 A * | 3/1992 | McLaren | ............... | A61B 17/72 606/304 |
| 5,263,955 A * | 11/1993 | Baumgart | .......... | A61B 17/7216 606/62 |
| 5,415,660 A * | 5/1995 | Campbell | .......... | A61B 17/7216 606/62 |
| 5,516,335 A * | 5/1996 | Kummer | ............ | A61B 17/7216 606/63 |
| 6,117,162 A * | 9/2000 | Schmieding | ....... | A61B 17/0401 606/232 |
| 6,336,929 B1 * | 1/2002 | Justin | ................. | A61B 17/7216 606/63 |
| 6,524,313 B1 * | 2/2003 | Fassier | ................... | A61B 17/72 606/63 |
| 7,063,706 B2 * | 6/2006 | Wittenstein | ........ | A61B 17/7216 606/90 |
| 7,857,832 B2 * | 12/2010 | Culbert | .............. | A61B 17/1637 606/246 |
| 8,137,349 B2 * | 3/2012 | Soubeiran | .......... | A61B 17/7216 606/63 |
| 8,777,947 B2 * | 7/2014 | Zahrly | ............... | A61B 17/7216 606/62 |
| 9,931,145 B2 * | 4/2018 | Martin | ............... | A61B 17/7208 |
| 2009/0254129 A1 * | 10/2009 | Tipirneni | ............. | A61B 17/742 606/309 |
| 2010/0036440 A1 * | 2/2010 | Morris | ................... | A61B 17/72 606/320 |
| 2010/0087820 A1 * | 4/2010 | Mantovani | ............. | A61B 17/72 606/62 |
| 2012/0209265 A1 * | 8/2012 | Pool | .................... | A61B 17/1725 606/55 |
| 2014/0214034 A1 * | 7/2014 | Rayes | ................ | A61B 17/8685 606/65 |
| 2016/0331421 A1 * | 11/2016 | Little | .................. | A61B 17/7002 |
| 2018/0042651 A1 * | 2/2018 | Little | ................. | A61B 17/7216 |

* cited by examiner

TELESCOPIC NAIL

CROSS REFERENCE TO RELATED APPLICATIONS

This is a National Stage of International Application No. PCT/TR2016/050130, filed Apr. 29, 2016, which claims the priority of Turkish Application No. 2015/05232, filed Apr. 29, 2015, the entire disclosures of which are hereby incorporated by reference in their entirety.

BACKGROUND OF THE INVENTION

1. Field of the Invention

The current invention is about intramedullary nails which are used in 18 months and above aged Osteogenesis Imperfecta diagnosed childrens long bones deformity correction, fracture stabilization and preventing fracture, for lengthening together with external fixators.

The Invention is especially about telescopic nails that, consists of 3 parts, is easy to use, can be placed inside the bone without damaging it too much, has extendable telescopic structure.

2. Description of the Prior Art

It differs from aspects such as the fractures of children and adult, growth factor, thick periosteum, reconstruction force and the effect of age. According to this, the treatment method is selected.

The application of the Intramedullary nailing of fractures of the children are different then the adults. The treatment of childrens long bone fractures with intramedullary nailing is increasing. The reason of this is the developing made on the intramedullary nails.

There is a need of developing intramedullary nails. The reason of this is the need of a development of an intramedullary nail system for Osteogenesis Imperfecta diagnosed children's long bone deformity corrections, fracture stabilization and preventing fracture, for lengthening together with external fixators.

The nail must be placed inside the bone providing minimum damage to the bone structure The nail should not prevent the growing of the child and elongation of the bone. There is a need of a solution for an easiest way of implantation of the nail.

In the French Patent Application, belonging to year 2001 with the FR2831421 number and A61B17/72 IPC-coded, is mentioned about a solution that is a medullary nail for baby leg which could be locked as a nail and has telescopic parts that could be regulated as the child grows. It provides a solution that at the end of the implant fits into a threaded hole of a plate with a threaded shaft. But it is not a suitable solution because of the implantation difficulties and the high level of damage to the bone.

SUMMARY OF THE INVENTION

The goal of the invention was prepared as in the prior technique, to develop Telescopic intramedullary nail which has an extendable telescopic structure, with an elimination of the negativities in the existing structure, easy to use and can be implanted into the bone without too much damage.

Another object of the invention is that the doctor's development of an easy solution that not effects the growing process of the child's bone.

Another aim of the present invention is, according to the telescopic structure consist of D-shaped female component and male component, the automatic self adaptation to the bone growth.

Another object of the invention is the minimal damage to the bone given by the corkscrew tip that is fixed to the front of the male component, while placing it into the bone.

Another object of the present invention is that various structures for fixing can be placed on to the Corkscrew tip or to the end cap.

Another object of the invention is easy to apply, owing to the two different types of female components as needed to develop a solution that can be used in an angled position.

In order to achieve the mentioned aims, telescopic intramedullary nail has been developed that provides many advantages.

Figure 1:
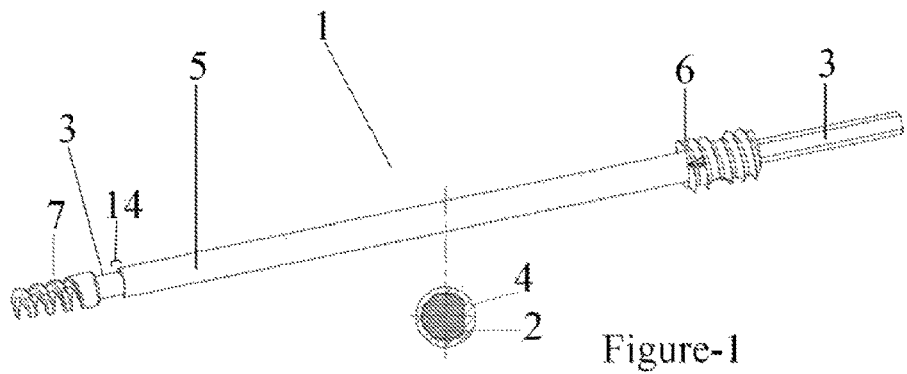
FIG. 1, A representative application of the invention is an indicated drawing of the implementation.
Figure 2:
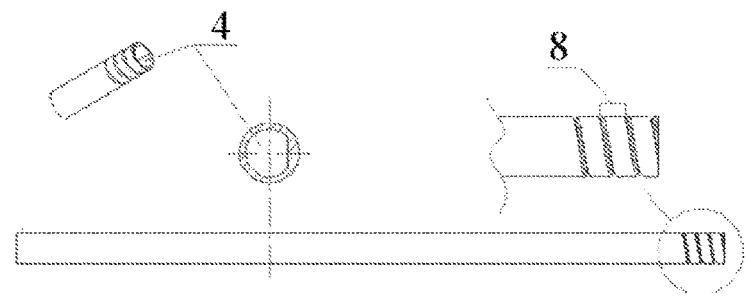
FIG. 2, A representative application of the invention is an indicated drawing of the female components internal structure and the threads on it.
Figure 3:
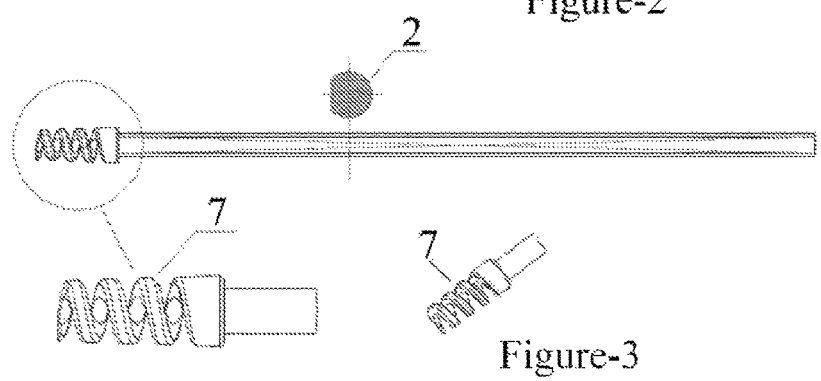
FIG. 3, A representative application of the invention is an indicated drawing of the male components internal structure and the corkscrew tip on it.
Figure 4:
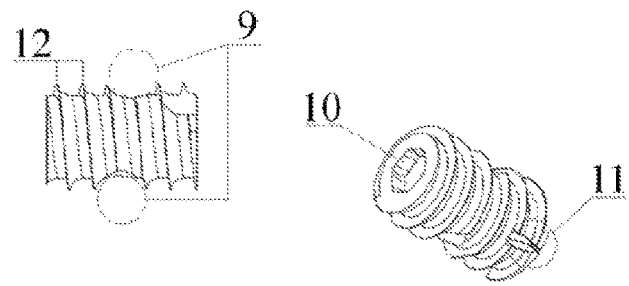
FIG. 4, A representative application of the invention is an indicated drawing of the structure of the screwdriver.
Figure 4:
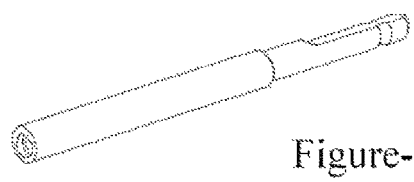
Figure 5:
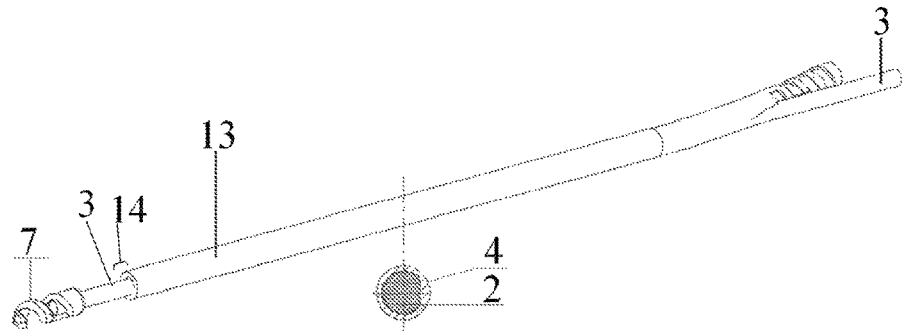
FIG. 5, A representative application of the invention is an indicated drawing of the telescopic nail that is generated with the angled female component.
Figure 6:
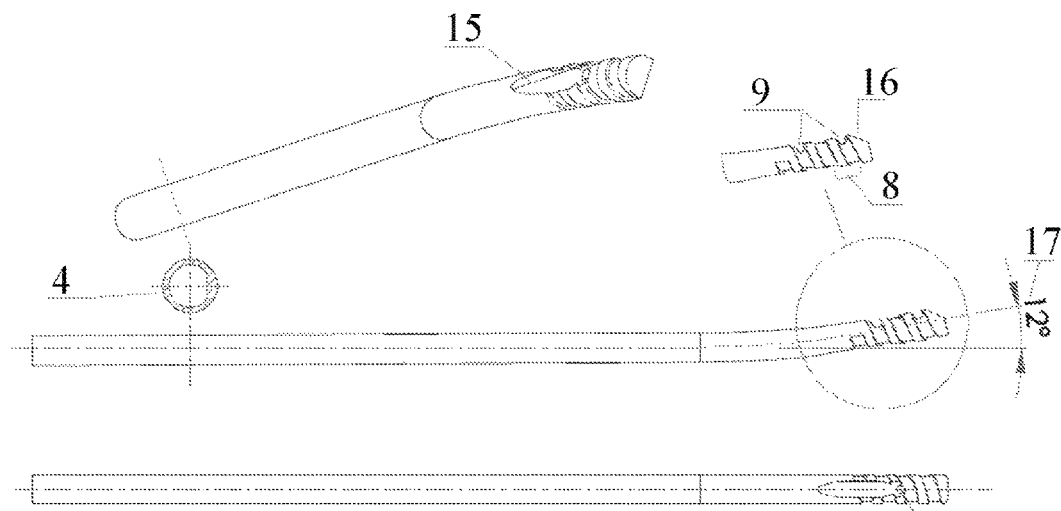
FIG. 6, A representative application of the invention is an indicated drawing of the angled female components internal structure and the threads on it.
Figure 7:
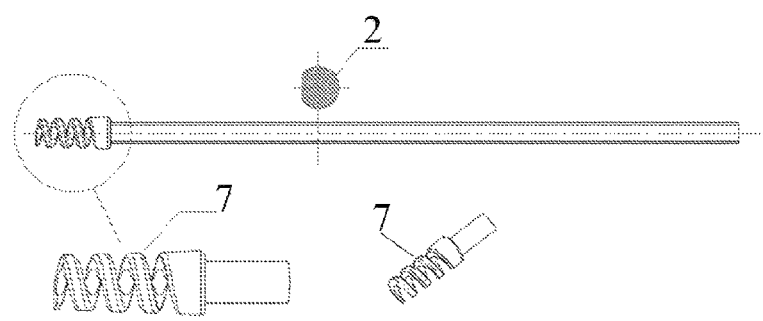
FIG. 7, A representative application of the invention is an indicated drawing of the internal structure of the male component mounted to angled female component the corkscrew tip on it.
Figure 8:
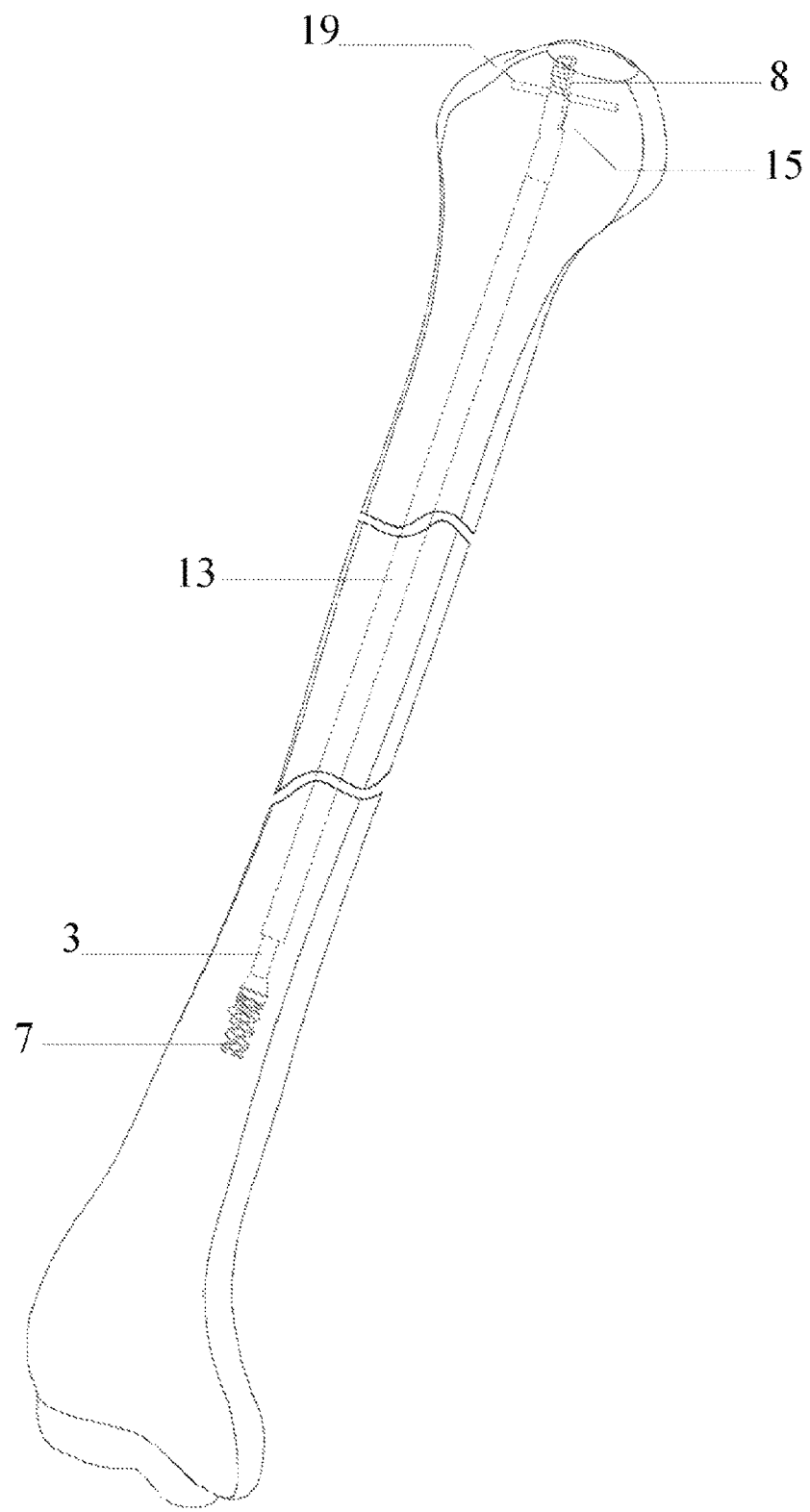
FIG. 8, A representative application of the invention is an indicated drawing of the application into the bone.
Figure 9:
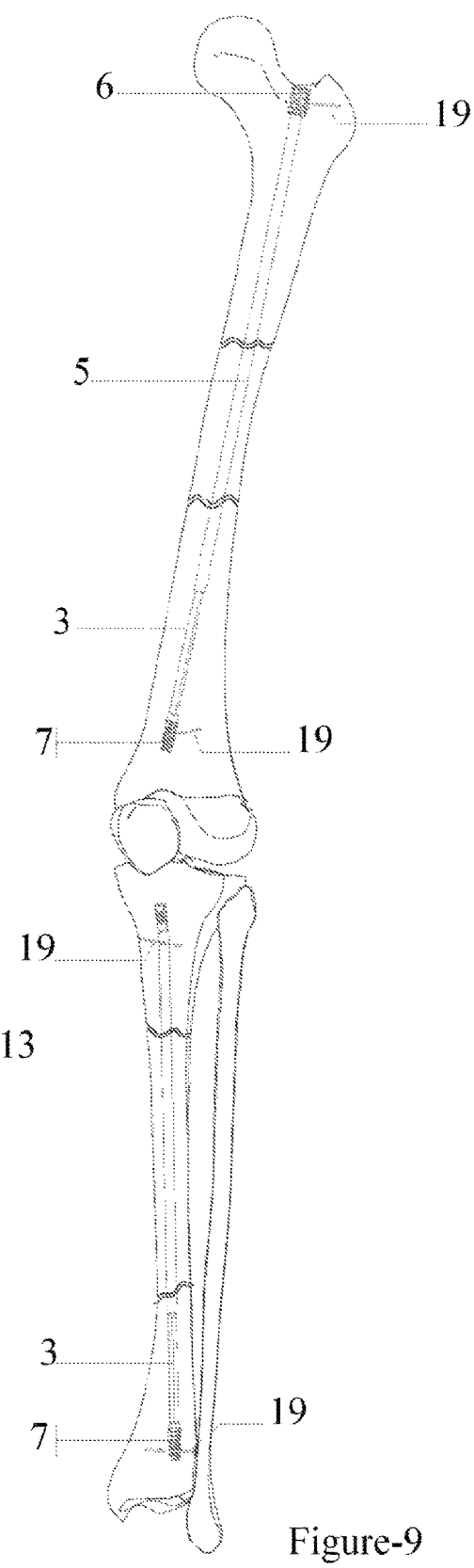
FIG. 9, A representative application of the invention is an indicated drawing of the application of the telescopic nail, that is generated with the angled female component, into the bone.

| DESCRIPTION OF THE REFERENCE NUMERALS | |
|---|---|
| 1 | Telescopic nail |
| 2 | D profile bar |
| 3 | Bar (male component) |
| 4 | D profile tube |
| 5 | Tube (female component) |
| 6 | End Cap |
| 7 | Corkscrew tip |
| 8 | Thread |
| 9 | Groove |
| 10 | Screwdriver |
| 11 | Self-Tapping |
| 12 | Cancellous |
| 13 | Angled tube (female component) |
| 14 | Telescopic structure |
| 15 | Slot (opening) |
| 16 | Cut |
| 17 | Angled part |
| 18 | Hole |
| 19 | Kirschner wire |

DETAILED DESCRIPTION OF A PREFERRED EMBODIMENT

Invention subject telescopic nail (1) can be fabricated from titanium or medical steel. Consists of 3 parts; one D profile Bar (2), bar (male component), suitable D profile tube (4), tube (female component) and an end cap (6) which is connected to the proximal part of the tube (5). D profile bar (2) and D profile tube (4) hinders rotation in telescopic nail (1). It can be formed in 2 different form as straight formed tube (female component) (5) and angled tube (female component) (13).

Owing to the telescopic structure, so that the straight formed female component (5), the angled female component (13) and the male components (3) can be nest, so without any hindering grows together with the child's bone.

Angled telescoping nail (1), consisting of angled female component (13) can be applied from the proximal of the humerus and tibia while the telescopic nail, consist of the straight formed female component, can be performed from the proximal and the distal of the femur. In this way the advantage of multi purpose usage are provided.

There is a corkscrew tip located at the distal end of the male component which is special designed to hold the bone in the best way and to give minimal damage to the growth cartilage. The end cap (6) is placed on the proximal of the female component (5) where the threads (8) are. The end cap (6) fixes the female component (5) to the bone with its self-tapping (11) cancellous (12) threads with the hexagonal screwdriver (10). For fixing more strongly and to prevent the slipping backward of the end cap (6), kirschner wires (19) and screws can be sent to the grooves (9). In this way the female component (5) and the male component (3) is fixed to the bone behind the growth plate at the distal and proximal epiphyseal part.

It has an angled female component (13) and D profile tube (4) with 12 degree angled upper end part developed for tibia and humerus. There is a Slot (opening) (15) at the beginning of the angled portion on which the male component (3) can come out. It has two slots (9) at the angled part (17) for fixing with screws or Kirschner wires (19) and a hole (18) for fixing with Kirschner wires (19). There is a thread (8) where the end cap (6) screws on and a cut (16) that prevents the flooding out of the bone.

1. Step: From the tip of the trochanter major at the proximal femur, approximately 2 cm incision is performed. 2. Step: From the tip of the trochanter major at the proximal femur a guide wire is advanced into the medullary canal. 3. Step: The osteotomy is applied at the center of rotation and angulation (CORA) of deformity (the point where the guide wire tap cortex) then the guide wire is advanced distally. 4. Step: If necessary the second osteotomy is done. The guide wire is advanced to distal segment until the epiphyseal bone. 5. Step: Reaming is began with the smallest cannulated reamer over the wire and the reaming process is done until metaphysis, do not perforate to epiphysis. 6. Step: The male component (3) is forwarded by turning clockwise through to the distal segment. 7. Step: After passing the osteotomy level, the distance between the corkscrew tip (7) and the joint surface is measured with the fluoroscopy. 8. Step: The length of the outer part of the male component (3) the level of fossa trochanterica is controlled by fluoroscopy. The distance between the corkscrew tip (7) and the joint surface which was measured at the previous step is left and the exceeding part is cut. 9. Step: Appropriate size of the Female component (5) of the telescopic nail (1) is chosen and entered into the proximal femur by sliding over the male component (3). 10. Step: By turning the female nail holder which is mounted to the threads (8) at the proximal part of the female component (5), the male component (3) is advanced through the medullary canal. The corkscrew tip (7) is placed to the distal metaphysis under the control of fluoroscopy. 11. Step: The end cap (6) is placed on the proximal part of the female component (5) while the thread (8) at the proximal part is outside. 12. Step: The female component (5) should be send without turning until the screw part touches the bone. The turning process is began when the end cap (6) touches the trochanteric fossa and to provide passing into the bone. In this stage the placement of the corkscrew tip (7) of the male component (3) to the distal epiphysis should be controlled. 13. Step: The fixation to the distal epiphysis is increased by sending two threaded Kirschner wire into the corkscrew tip (7). 14. Step: Extra locking screws from the notch on the proximal locking screws (3) can be applied to increase stability.

Alternative surgical technique steps are as follows;

1. Step: In cases where the medullary canal is closed, the procedure is began with osteotomy that is applied to center of the deformity rotation and angulation (CORA). After the osteotomy the guide wire is entered from the center point of the osteotomy line and advanced to the proximal. After fluoroscopic control the canal is opened with an appropriate reamer. 2. Step: The distal part of the bone is made visible at the osteotomy line. The guide wire is send from the distal to the medullary canal. The wire end must reach the distal epiphysis. If the wires contact the cortex or remove because of the bone curve, a second osteotomy is done and the wire is orientated to the center of the bone. 3. Step: After this step, the operation is continued by passing to Step 6 of the techniques which is described above.

Straight shaped female component (5), angular female component (13) and the male component (3) nests in telescopic structure (14) and grows together with the child's bone without any hindering, the male component (3), straight formed female component (5) and angular female component (13) forms the telescopic nail (1), has at least one corkscrew tip (7) that allows to enter the bone with a minimal damage.

The male component (3), straight formed female component (5) and angular female component (13) have one end cap (6) that mounts to the threads at the upper end.

The end cap (6) that fixes the female component (5) to the bone with its self-tapping (11) cancellous (12) threads with a hexagonal screwdriver (10), the male component (3), straight formed female component (5) and angular female component (13), has at least one kirschner wire (19), fixing part that fixes corkscrew tip (7) and/or end cap (6).

Has at least one corkscrew tip located at the distal part of the male component that holds the bone in the best way and gives minimal damage to the growth cartilage.

An angled telescopic nail (1) solution, that is applied from the proximal of the Tibia and Humerus and composed of an angled female component (13), a telescopic nail (1) solution, that is applied from the distal or the proximal part of the Femur and composed of straight formed female component (5), has been developed.

D profile tube with 12 degree angled (4) upper end part and an angled female component (13) has a slot (opening) (15) at the beginning of the angled part (17) on which the male component (3) can come out, has two slots (9) at the angled portion (17) for fixing with screws or Kirschner wires (19) and a hole (18) for fixing with Kirschner wires (19), has a thread (8) where the end cap (6) screws on and a cut (16) that prevents the flooding out of the bone.

Have Kirschner wires (19) or screw that can be sent to the grooves (9) at the side of the end cap (6), to prevent slipping back of the screw and to strengthen the fixation.

The invention claimed is:

1. An intramedullary nail for use with growing patients aged at least eighteen months old for the purpose of correcting bone deformity, stabilizing bone fractures, and preventing bone fractures, the intramedullary nail comprising:
    at least one male component that is nested within a female component in a slidingly telescopic manner such that the male and female components can extend with respect to each other as the patient grows and the intramedullary nail does not hinder bone growth;
    at least one corkscrew tip secured to one male component to permit entry into a bone with minimal damage, the at least one corkscrew tip comprising a helical body portion and being free of a centrally-located shaft, the corkscrew tip having a void that extends axially along a portion of the length of the corkscrew tip, and the helical body portion comprises an extended member which is wound helically around the void;
    the male component having a straight portion at an end thereof opposite from the corkscrew tip; and
    the female component having an angled portion at an upper end thereof which is located at an opposite end of the intramedullary nail from the corkscrew tip, the angled portion of the female component having a slotted opening through which the straight portion of the male component can extend therethrough.

2. The intramedullary nail of claim 1 wherein the female component has threads at the upper end thereof, and an end cap is mounted to the threads.

3. The intramedullary nail of claim 2 wherein the end cap is configured to fix the female component to the bone with self-tapping cancellous threads with a hexagonal screwdriver; and
    the nail further comprises at least one kirschner wire for fixing the corkscrew tip and/or the end cap within the bone.

4. The intramedullary nail of claim 2 wherein the end cap includes grooves, and there is also provided Kirschner wires or a screw that can be secured to the grooves along a side of the end cap to prevent the end cap from slipping back and to strengthen the fixation.

5. The intramedullary nail of claim 1 including an end cap that is configured to fix the female component to the bone with self-tapping cancellous threads with a hexagonal screwdriver; and
    at least one kirschner wire for fixing the corkscrew tip and/or the end cap within the bone.

6. The intramedullary nail of claim 1 wherein the corkscrew tip is located at a distal end of the male component.

7. The intramedullary nail of claim 1 wherein the female component has a straight portion that is configured for placement in either the distal or the proximal part of a femur.

8. The intramedullary nail of claim 1 wherein the intramedullary nail having the female component with the angled portion is configured for placement in the proximal part of the tibia or humerus.

9. The intramedullary nail of claim 1 wherein the angled portion of the female component is angled at 12 degrees.

10. The intramedullary nail of claim 1 wherein an outer surface of the male component and an inner surface of the female component each have a non-circular cross-section such that the male component and the female component cannot rotate with respect to one another.

11. The intramedullary nail of claim 10 wherein an outer surface of the male component and an inner surface of the female component each have a "D"-shaped cross-section.

* * * * *